United States Patent [19]

Veatch

[11] 4,294,260
[45] Oct. 13, 1981

[54] CYSTOURETHROGRAPHIC EXAMINATION CHAIN

[75] Inventor: William M. Veatch, Olympia, Wash.

[73] Assignee: Olympia Radiological Associates, Olympia, Wash.

[21] Appl. No.: 49,503

[22] Filed: Jun. 18, 1979

[51] Int. Cl.³ .............................................. A61B 6/00
[52] U.S. Cl. .................... 128/654; 128/774; 63/2
[58] Field of Search ................. 128/653–654, 128/772, 774, 788, 348; 250/312; 46/138, 139, 161; 63/2

[56] References Cited

U.S. PATENT DOCUMENTS

| | | | |
|---|---|---|---|
| 8,736 | 3/1835 | Harrington | 128/788 |
| 1,455,993 | 5/1923 | Conway | 63/2 |
| 1,567,021 | 12/1925 | Detlefsen et al. | 63/2 |
| 2,833,249 | 5/1958 | Cornman | 119/109 |
| 3,369,542 | 2/1968 | Thaidigsman | 128/654 |
| 3,794,041 | 2/1974 | Frei et al. | 128/348 |
| 3,844,274 | 10/1974 | Nordstrom | 128/654 |
| 4,111,190 | 9/1978 | Plumridge | 128/658 |

Primary Examiner—Kyle L. Howell
Attorney, Agent, or Firm—Seed, Berry, Vernon & Baynham

[57] ABSTRACT

A cystourethrographic chain for insertion into the urethra and bladder of a patient. A cystourethrographic chain having a flexible inner tensioning member with a smoothly contoured forward stop and a rearward stop fastened thereto. A plurality of radio opaque beads are slidably mounted on the chain between the forward and rearward stops.

2 Claims, 4 Drawing Figures

CYSTOURETHROGRAPHIC EXAMINATION CHAIN

BACKGROUND OF THE INVENTION

1. Field of the Invention

This invention relates to apparatus for inserting a urethral chain into the female urinary uretha and bladder for cystourethrographic examination.

2. Description of the Prior Art

Chain cystourethrography is a well established radiographic procedure that accurately depicts the urethrovesical relationship in women with stress incontinence. Heretofore, an ordinary round bead chain is placed in the urethra usually via a short segment of rubber catheter which has been split longitudinally to allow its removal after the chain is in position. This procedure is clumsy, can be painful and requires the services of a highly skilled medical practitioner. Efforts to improve on the rubber catheter type of chain insertion are also known. U.S. Pat. Nos. 3,369,542 and 3,844,274 and 4,111,190 are all directed to techniques for inserting the bead chain into the urethra. Each of these prior art devices, however, requires encapsulating or covering the chain with a separate catheter or using forceps to make the insertion. As a result, the techniques of these patents still remain clumsy and cause considerable discomfort to the patient.

SUMMARY OF THE INVENTION

It is an object of this invention to provide apparatus for inserting a cystourethrographic chain directly into a patient without the use of external covering or insertion mechanisms.

It is another object of this invention to provide a flexible cystourethrographic chain which can be self-rigidifying merely by manipulative pressure on the chain itself.

Basically the method of this invention includes the step of rigidifying the uncovered chain which has a smoothly contoured forward end, pushing the rigidified chain directly into and against the walls of the urethra and into the bladder, and then relaxing the chain for the examination.

Basically the chain of this invention includes an elongated continuous flexible tensioning member having a forward stop fastened to an end thereof with the forward stop having a smoothly contoured forward end. A rearward stop is fastened to the opposite end of the tensioning member and a plurality of radio opaque bead members are slidably mounted on the tensioning member between the stops so that by pressing the bead members forward against the forward stop the chain will be rigidified.

As is readily apparent, the method and the chain provide a technique in which insertion of the chain can be made by a non-skilled practitioner and since the insertion is directly made into the urethra without external devices or forceps or the like the chain, once inserted, will relax to follow the shape and angular relationship of the urethra without further discomforting manipulations by the medical practitioner. Thus, the cystourethrographic examination requires less time to perform and less discomfort to the patient.

DETAILED DESCRIPTION OF THE PREFERRED EMBODIMENTS

Figure 1:
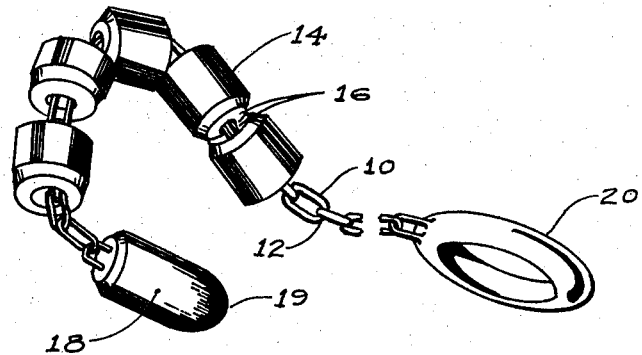
FIG. 1 is an isometric view of a flexible chain embodying the principles of the invention.
Figure 2:
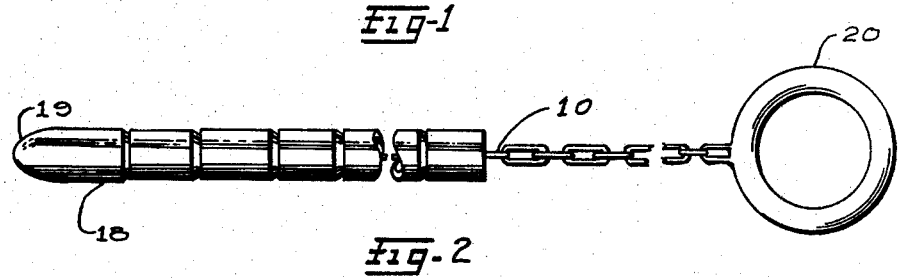
FIG. 2 is a side elevation of the chain shown in FIG. 1 with the chain in a rigid condition.
Figure 3:
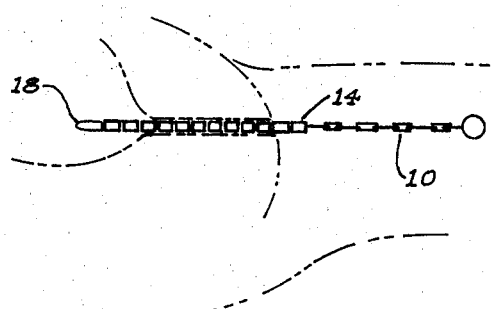
FIG. 3 is an operational schematic showing insertion of the rigidified chain into the urethra of a patient.
Figure 4:
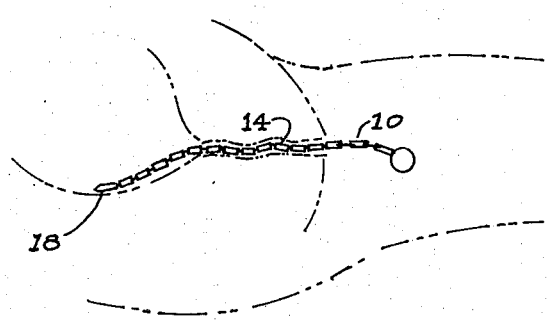
FIG. 4 shows the chain in a relaxed condition within the patient.

The chain includes an elongated flexible tensioning member 10 preferably in the form of interconnected metallic chain links 12. Preferably the tensioning member is approximately 17 centimeters in length and can be made from fine jeweler's chain. Slidably mounted on the chain are a series of barrel shaped bronze beads 14 having flattened opposite ends 16.

A stop 18 is fastened to a forward end of the chain and is provided with a smoothly contoured nose 19. The opposite end of the chain is fastened to a rearward stop preferably in the form of a ring 20. In the preferred embodiment the bronze beads are 3 millimeters in diameter and approximately 3.5 millimeters in length. Preferably, the chain and the beads are metallic so as to be radio opaque to X-ray but any materials which would be visible on X-ray and capable of being sterilized would suffice.

Gentle traction at the end or mid-portion of the chain while pushing the beads against the forward stop produces sufficient rigidity to allow ready urethral insertion into the patient. When the pressure is relaxed, the chain conforms nicely to the urethral contour.

One procedure successfully employed is to insert the chain after retrograde installation of about 30 cc of contrast agent into the bladder. Erect lateral radiographs during straining permit measurement of the posterior urethrovesical angle and the angle of urethral inclination in the usual manner. AP views are occasionally useful.

While the preferred embodiment of the method and apparatus have been illustrated in the drawings, it should be understood that variations will be apparent to one skilled in the art without departing from the principles herein. Accordingly, the invention is not to be limited to the specific form illustrated in the drawing.

I claim:

1. A flexible insert for cystourethrographic examination, comprising:
    an elongated continuous radio opaque flexible tensioning member having a plurality of interconnected rigid chain links,
    a forward stop fastened to an end of the tensioning member and having a smoothly contoured continuous forward end,
    a rearward stop fastened to the tensioning member, and
    a plurality of radio opaque bead members having axially opposite flat ends slidably mounted on the chain links between said forward and rearward stops whereby pressing the bead members forward against the forward stop will push the flat ends of the beads together to rigidify the insert so that the forward stop can be pushed into the urethra and bladder of a patient.

2. The insert of claim 1, said rearward stop including a handle for grasping the tensioning member while pressing the beads forward and removing the insert from the urethra.

* * * * *